United States Patent [19]

Marois et al.

[11] Patent Number: 4,818,530

[45] Date of Patent: Apr. 4, 1989

[54] PREPARATION OF PELLETS CONTAINING FUNGI FOR CONTROL OF SOILBORNE DISEASES

[75] Inventors: James J. Marois, Davis, Calif.; Deborah R. Fravel, Silver Spring, Md.; William J. Connick, Jr., New Orleans; H. Lynn Walker, Ruston, both of La.; Paul C. Quimby, Jr., Leland, Miss.

[73] Assignee: The United States of America as represented by the Secretary of Agriculture, Washington, D.C.

[21] Appl. No.: 98,173

[22] Filed: Sep. 18, 1987

Related U.S. Application Data

[60] Division of Ser. No. 713,733, Mar. 20, 1986, Pat. No. 4,724,147, which is a continuation-in-part of Ser. No. 506,952, Jun. 22, 1983, abandoned.

[51] Int. Cl.$^4$ .................... A61K 63/00; A01N 63/04; A01N 37/18
[52] U.S. Cl. ......................... 424/93; 71/79; 71/118; 514/54
[58] Field of Search ................ 424/93; 514/54; 71/79

[56] References Cited

U.S. PATENT DOCUMENTS

| | | | |
|---|---|---|---|
| 2,441,729 | 3/1948 | Steiner | 71/79 |
| 3,649,239 | 3/1972 | Mitchell | 71/63 |
| 3,849,104 | 11/1974 | Daniel et al. | 71/79 |
| 3,999,973 | 12/1976 | Templetion | 71/79 |
| 4,053,627 | 10/1977 | Scher | 424/278 |
| 4,390,360 | 6/1983 | Walker | 71/79 |
| 4,401,456 | 8/1983 | Connick, Jr. | 71/79 |
| 4,419,120 | 12/1983 | Walker | 71/79 |
| 4,718,935 | 1/1988 | Walker et al. | 424/93 X |
| 4,724,147 | 2/1988 | Marois et al. | 424/93 |

FOREIGN PATENT DOCUMENTS

| | | | |
|---|---|---|---|
| 0097571 | 1/1984 | European Pat. Off. | 424/93 |
| 1942161 | 2/1970 | Fed. Rep. of Germany | 424/93 |
| 161312 | 12/1981 | Japan | 424/93 |

OTHER PUBLICATIONS

Jung et al., Chem. Abstracts, vol. 97, 71457t, (1982).
Marois et al., Plant Disease 66:1166–68 (1982).
Fravel et al., Phytiophology, 74(6)–756, (Mar. 21, 1984).
Fravel et al., Phytiopathology, 75, 774–777 (1985).

*Primary Examiner*—Howard E. Schain
*Attorney, Agent, or Firm*—M. Howard Silverstein; Raymond C. Von Bodungen; David G. McConnell

[57] ABSTRACT

This invention relates to a method for preparing pellets containing living biocontrol fungi. Fungi are selected and grown for sufficient time to produce inoculum. The fungal propagules are harvested, homogenized and diluted with sodium alginate solution. Pelletization is then accomplished by dropwise addition of the fungal propagule-alginate mixture into a solution of calcium chloride or calcium gluconate. The resultant alginate gel pellets containing living fungi can then be dried and are used to inoculate agricultural fields infested with soilborne plant diseases.

16 Claims, No Drawings

PREPARATION OF PELLETS CONTAINING FUNGI FOR CONTROL OF SOILBORNE DISEASES

CROSS-REFERENCE TO RELATED APPLICATIONS

This is a continuation-in-part of application Ser. No. 506,952, filed June 22, 1983, now abandoned.

BACKGROUND OF THE INVENTION (1) Field of the Invention

This invention relates to formulations of inoculum of microorganisms.

(2) Description of the Prior Art

Antagonistic fungi in several genera have been previously shown to effectively control plant disease caused by pathogenic fungi. *Talaromyces flavus* is used to control Verticillium wilt of eggplant which is caused by *Verticillium dahliae* (J. J. Marois, et al., 1982. Plant Disease 66:1166-1168). Since eggplant is usually subjected to transplanting, *T. flavus* is applied as a drench before transplanting takes place.

Potatoes and cotton are other examples of economically important crops which are also subject to *V. dahliae*. Since potatoes and cotton are both seeded directly into the field, the drench formulations are not practical. However, dust formulations of *T. flavus* have been used to treat potato seed pieces but this is inefficient because the dust easily blows away. In addition, the dust is not adequately distributed in the root zone where it is most needed to protect the roots from the pathogen.

Connick, Jr., (U.S. Pat. Nos. 4,401,456 and 4,400,391) both disclose processes for incorporating chemical, non-living, bioactive materials in alginate gels. Connick, Jr., (4,401,456 and 4,400,391) discloses chemicals which are formulated to kill living matter. He also teaches the use of cations in the process, i.e. barium, copper, lead, zinc, all of which would be reasonably expected to kill any living fungi incorporated into the alginate gel.

The use of alginate gel technology to formulate agricultural products, pesticides and food items has also been disclosed. For example, U.S. Pat. No. 4,053,627 describes the use of alginate gel discs for mosquito control, U.S. Pat. No. 3,649,239 discloses fertilizer compositions, and U.S. Pat. No. 2,441,729 teaches the use of alginate gels as insecticidal as well as candy jellies. None of these patents disclose any method for incorporating living materials or fungi into an alginate gel matrix.

SUMMARY OF THE INVENTION

Pelletization of living biocontrol fungi useful to control selected plant disease using aqueous solutions of sodium alginate, calcium gluconate and calcium chloride is disclosed. The granular formulations of living fungi produced by this method have extended shelf life and sustained release or sustained production characteristics.

The method comprises the following steps in combination: selecting and growing fungi for sufficient time to be used as inoculum, harvesting and homogenizing the fungal propagules for sufficient time to uniformly mix the propagules, and diluting the fungus propagule homogenate with a sodium alginate solution with a sufficient concentration of sodium alginate to effect adequate gelation. This mixture is then added dropwise to a solution of $CaCl_2$ or calcium gluconate, thus forming alginate gel pellets which contain fungus dispersed throughout.

U.S. Pat.s Nos. 4,401,456 and 4,400,391 teach a process for incorporating chemical bioactive materials in alginate gels. There is no teaching in said patents on, nor is there anticipated, the incorporation of living fungi as active materials. Indeed, one skilled in the art might expect fungi to die or become ineffective as a result of being incorporated in alginate pellets. The chemical bioactive materials of said Pat. Nos. 4,401,456 and 4,400,391 are released from the products by virtue of their water solubility (leaching or diffusion) or as a result of biodegradation of the alginate matrix. This is totally different from the growth and release of active propagules from a living fungus.

It was completely unexpected that a living fungus could be incorporated in alginate gel pellets or granules to give an effective material. For example, barium chloride and cupric chloride are among the preferred water-soluble metal salt gellants taught by U.S. Pat. Nos. 4,401,456 and 4,400,391 for use with chemical bioactive materials, but these salts are fungitoxic when used in the process of the present invention. Other reasons why it is not obvious to use the teachings of U.S. Pat. Nos. 4,401,456 and 4,400,391 to produce effective fungus-containing pellets are stated below.

All mechanisms known for biocontrol by fungi (competition, antibiosis and parasitism) require an actively metabolizing antagonist. Hence, the effectiveness of biocontrol fungi pelletized in an alginate matrix could not be expected since propagules of the fungi must grow free of the matrix to control pathogenic fungi.

The ability of the biocontrol fungi to survive the process of the present invention could not be predicted a priori because one would have expected the osmotic shock resulting from addition of the liquid alginate suspension into the calcium salt to kill the biocontrol fungi.

Stability of alginate gel pellets containing living fungi is very important for commerical reasons. The biocontrol fungi must survive for extended shelf life periods of time to meet shipping needs and agricultural uses. Furthermore, other contaminant microorganisms are also pelletized along with the desired fungi during the formulation process. Since many microorganisms may be capable of competing with the desired fungi, the recovery and growth of the desired fungi after storage was impossible to predict beforehand. Applicants' biocontrol fungi-containing pellets produced living colonies of fungi when applied to an agricultural environment after extensive shelf life periods of time. This was totally unpredictable.

In addition to its use in control of plant pathogens, the method of sodium alginate formulation described by applicants' preferred embodiment has other applications. For example, the production of inoculum of plant pathogens would facilitate uniform infestation of an area with a pathogen to evaluate host resistance, control methods, or to perform epidemiological research.

DESCRIPTION OF THE PREFERRED EMBODIMENTS

Soilborne diseases of agricultural crops can be controlled by the following biocontrol fungi:

*Gliocladium virens* isolate Gl3 (NRRL #15937)
*Penicillium oxalicum* isolate Windels {NRRL #15938) (ATCC #52658)

Talaromyces flavus isolate Tf-1 (NRRL #15935) (ATCC #52201)
Talaromyces flavus biotype Tfl-1 (NRRL #15936)
Trichoderma viride biotype T-1-R9 (ATCC #52442) (U.S. Pat. No. 4,489,161).

All, except the *T. viride*, are on deposit with the Agricultural Research Culture Collection (NRRL) and available from: A. J. Lyons, Curator, ARS Patent Collection, Culture Collection Research, NRRC, 1815 N. University Street., Peoria, Ill., 61605. In addition, the *P. oxalicum*, *T.flavus* Tf-1, and the *Trichoderma viride* are also on deposit with: American Type Culture Collection, Rockville, Md. In addition, the *T. viride* T-1-R9 is a genetically manipulated biotype and has been patented (U.S. Pat. No. 4,489,161).

Each of the five fungi are cultured and pelletized separately to demonstrate the flexibility of the process. Since two of the fungi produced two distinct types of spores, they are also pelletized separately to demonstrate further flexibility. The versatility of the process is also demonstrated by using two different biotypes of the same fungus.

Ascospores are produced by growing *T. flavus* on potato-dextrose agar for 4 weeks at 30° C. in the dark. When *T. flavus* is grown on a molasses-corn steep medium (a more carbon rich medium) in the light at 25 C for 1 week, conidia are produced. Conidia of G. virens are produced by growing the fungus on V-8 juice agar for 1 week at 25° C. Conidia of *P. oxalicum* and *T. viride* are produced by growing the organisms on potato-dextrose agar for 1 week at 25° C. Other microbiological media are also suitable and can even be incorporated into the pellets along with the propagules. Experimental details for growing the fungi are given in the article "Biological Control of Verticillium wilt of eggplant in the field," by J. J. Marois, et al., Plant Disease. 66:1166–1168 (1982).

Propagules of the fungi are dislodged from the agar surface by rubbing, suspended in water, then comminuted in a Sorval mixer or similar apparatus to insure uniform distribution of the propagules. The alginate solution which contains 10 g of sodium alginate, 100 g of pyrophyllite, and 1 L of water is mixed for one minute in a blender and then various concentrations of propagules in water are added. The resulting mixture is then added dropwise to a salt solution of either 0.25 M $CaCl_2$ or 0.1 M $C_{12}H_{22}CaO_{14}$ (calcium gluconate) in distilled water. Pellets form almost immediately upon contact with the salt solution. The salt solution is decanted and the pellets are dried. Drying to a 5% to 15% moisture content is preferred. Pellets can be disintegrated in mixture of $8.7 \times 10^{-3}$ M. $KH_2PO_4$ and $3.0 \times 10^{-2}$ M. $Na_2HPO_4$ (pH 7.7) and assayed by dilution plating to determine viable propagule population. Sodium alginate is the preferred alginate but other water soluble salts of alginic acid such as potassium alginate may be used. Sodium alginate concentration in the propagule-sodium alginate-pyrophyllite-water mixture can be from 0.5 to 2.0% (w/v) but the preferred concentration is 0.75 to 1.0%, A water soluble calcium salt such as calcium chloride or calcium gluconate is necessary for gelation of sodium alginate solutions, and these compounds are not toxic to the fungi. An effective concentration range of the calcium chloride or calcium gluconate bath, also called the salt or gellant solution, is 1% to 15% (w/v), but 2% to 5% is preferred. Gelation proceeds faster as the concentration of the salt solution is increased.

Various organic and inorganic fillers such as clays, diatomaceous earth, sand, or corn cobs can be used in the formulations of the present invention. Pyrophyllite (hydrous aluminum silicate) is preferred in quantities up to about 20% (w/v) because it has a neutral pH. Other adjuvants that may be of use when incorporated in formulations are: selective fungistats, antibiotics, nutrients, materials that stimulate spore production, viscosity modifiers, and materials to control hardness of the pellets or their rate of biodegradation or disintegration.

The simplicity of the requirements for carrying out the process of the present invention permits much latitude in equipment design. A suitable apparatus, described only for the purpose of illustration and not to be construed as limiting to the invention, consists of a reservoir to contain the alginate-propagule-prophyllite mixture, a pump to feed this mixture, or a gravity-feed arrangement, from the reservoir to orifices about 1–2 mm in diameter that permit the mixture to be added in a dropwise manner into a gellant solution contained in any convenient vessel. The alginate gel pellets that form have propagules of the desired fungus incorporated throughout and are harvested from the gellant solution by any suitable means. The alginate gel pellets may be dried to form dried pellets or granules making them more suitable for storage and agricultural field use. A continuous process is possible involving the continuous removal of gel pellets and maintenance of an effective gellant solution concentration. It is also possible to extrude the alginate-propagule-pyrophyllite mixture into the gellant solution to form a string-like gel which could be further processed to make granules.

Most desired fungi should be processed below 50° C., preferably in the range of 15°–40° C. Dwell time of the gel pellets in the gellant solution can be from about 0.1 to 60 minutes, but 0.2 to 5 minutes is preferred.

The fungi reproduced when the gel pellets were placed in moist field soil or on appropriate microbiological media when brought into contact with moisture. Dried pellets may be stored for an extended period of time. (Table 1).

Pellets produced as described above have sustained-release characteristics and provide residual activity to enhance the performance of the biocontrol fungi. Applicants' preferred embodiment also provides a useful method for storing inoculum for extended periods of time.

The pathogens enumerated above, when formulated as dried pellets, reproduced readily under field conditions when adequate moisture was present and effectively controlled the targeted soilborne diseases.

Alginate formulations of biocontrol fungi may be applied directly to soil as pellets, or propagules can be produced on the pellets, then removed and applied to the desired environment using any compatible, effective means of distribution.

Formulation and production of alginate gel pellets containing the above-described living biocontrol fungi are readily illustrated in the following examples:

EXAMPLE 1

Ascospores of *Talaromyces flavus* isolate Tf-1 were produced by growing the fungus on potato-dextrose agar for 4 weeks in the dark at 30° C. Cleistothecia were removed by gently scraping the medium and were added to water and comminuted for 1 minute in a Sorvall mixer to insure disruption of cleistothecia and asci and produce a uniform distribution of ascospores. Ascospores were added to a mixture containing 1% by weight of sodium alginate and 10% of pyrophyllite in sufficient distilled water to total 200 ml in volume. The ascospores were added in concentrations ranging from $10^5$ to $10^8$ per ml of alginate suspension. The alginate-pyrophyllite-fungal propagule mixture was stirred and added dropwise from a reservoir through tubes (each terminating in a 1 mm diameter orifice), the droplets falling a distance of about 15 cm into 200 ml of a 0.25 M $CaCl_2$ gellant solution. Gel beads immediately formed, allowed to remain in the gellant solution for up to 45 minutes, separated by decanting, spread on aluminum foil, and dried to about 10% moisture content at ambient temperature using a gentle flow of air. About 22 g of pellets were obtained. Drying transformed the gel beads into hard granules or pellets which were stored under room conditions. Viable propagule populations were determined as follows: before pelletization, immediately following pelletization, 24 hours, 1,2,4,8, and 12 weeks. Results reported in Table 1 show that 100% of the fungus propagules survived during pellet formation.

EXAMPLE 2

Conidia of *Talaromyces flavus* isolate Tf-1 were produced by growing the fungus on molasses-corn-steep medium in the light at 25° C. for 1 week. The propagules were pelletized and viable populations of fungus propagules were determined as in Example 1 with results as reported in Table 1 which shows 100% survival during pellet formation.

EXAMPLE 3

Ascospores of *Talaromyces flavus* isolate Tf-1 were grown and pelletized as described in Example 1 except that 0.1 M calcium gluconate was used as the gellant solution and only one initial concentration of spores ($10^6$ per M alginate suspension) was pelletized. Viable populations of fungus propagules were determined as in Example 1 with results reported in Table 1 which shows 100% survival during pellet formation.

EXAMPLE 4

Conidia of *Talaromyces flavus* isolate Tf-1 were produced by growing the fungus on molasses corn-steep-medium in the light at 25° C. for 1 week. The propagules were pelletized as described in Example 1 except that 0.1 M calcium gluconate was used as the gellant solution. Only one initial concentration ($10^6$ per ml adequate suspension) was pelletized. Viable populations of fungus propagules were determined as in Example 1 with results reported in Table 1 which shows 100% survival during pellet formation.

EXAMPLE 5

Ascospores of *Talaromyces flavus* isolate Tfl-1 were grown and pelletized as in Example 1. Viable populations of fungus propagules were determined as in Example 1 with results reported in Table 1 which shows 100% survival during pellet formation.

EXAMPLE 6

Conidia of *Talaromyces flavus* isolate Tfl-1 were grown and pelletized as in Example 2. Viable populations of fungus propagules were determined as in Example 1 with results reported in Table 1 which shows 100% survival during pellet formation.

EXAMPLE 7

Ascospores of *Talaromyces flavus* isolate Tfl-1 were grown and pelletized as in Example 3. Viable populations of fungus propagules were determined as in Example 1 with results reported in Table 1 which shows 100% survival during pellet formation.

EXAMPLE 8

Conidia of *Talaromyces flavus* isolate Tfl-1 were grown and pelletized as in Example 4. Viable populations of fungus propagules were determined as in Example 1 with results reported in Table 1 which shows 100% survival during pellet formation.

EXAMPLE 9

Conidia of *Gliocladium virens* isolate Gl-3 were produced by growing the fungus on V-8 juice agar for 1 week at 25° C. Light was not excluded. Conidia were pelletized as described in Example 1. Viable populations of fungus propagules were determined as in Example 1 with results reported in Table 1 which shows 40–89% survival during pellet formation.

EXAMPLE 10

Conidia of *Gliocladium virens* isolate Gl-3 were grown on potato-dextrose agar and pelletized as described in Example 1 except that 0.1 M calcium gluconate was used as the gellant solution. Viable populations of fungus propagules were determined as in Example 1 with results reported in Table 1 which shows a 57% survival during pellet formation.

EXAMPLE 11

Conidia of *Penicillium oxalicum* were grown on potato-dextrose agar and pelletized as described in Example 1. Viable populations of fungus propagules were determined as in Example 1 with results reported in Table 1 which shows 100% survival during pellet formation.

EXAMPLE 12

Conidia of *Penicillium oxalicum* were grown on potato dextrose agar and pelletized as described in Example 1 except that 0.1 M calcium gluconate was used as a gellant solution. Viable populations of fungus propagules were determined as in Example 1 with results reported in Table 1 which shows 100% survival during pellet formation.

EXAMPLE 13

Conidia *Trichoderma viride* isolate T-1-R9 were grown on potato-dextrose agar and pelletized as described in Example 1. Viable populations of fungus propagules were determined as in Example 1 with results reported in Table 1 which shows 100% survival during pellet formation.

EXAMPLE 14

Conidia of *Trichoderma viride* isolate T-1-R9 were grown on potato dextrose agar and pelletized as described in Example 1 except that 0.1 M calcium gluconate was used as the gellant solution. Viable populations of fungus propagules were determined as in Example 1 with results reported in Table 1 which shows 100% survival during pellet formation.

The following examples demonstrate effective agricultural use of the above-described biocontrol fungi:

EXAMPLE 15

Pellets of *Talaromyces flavus* isolate Tf-1, as prepared in Example 1, were applied at a rate of 6.7 g pellets/100 row feet, in an agricultural field naturally infested with *Verticillium dahliae*. These furrows were then planted with potatoes. Incidence of Verticillium wilt was recorded 2 weeks prior to harvest. There was approximately 60% less wilt and 15% increase in the weight of marketable tubers in the *T. flavus*-pellet treated potatoes compared to nontreated replicates.

EXAMPLE 16

Pellets containing *Gliocladium virens* as prepared in Example 9 were incorporated into field soil naturally infested with Pythium and Rhizoctonia (causes pre- and post- emergence damping off disease). Pellets were incorporated at the rate of 0.5% (w/w). Radish seeds were planted and after 10 days there were nearly twice as many plants in the Gliocladium treated soil as compared to a control.

EXAMPLE 17

Pellets containing *Gliocladium virens* as prepared in Example 10 were tested for control of damping-off as described in Example 16. More than twice as many healthy seedlings survived using the pellets containing the biocontrol fungus than in the replicates receiving pellets made without fungus.

EXAMPLE 18

Pellets containing *Penicillium oxalicum* as prepared in Example 11 were tested for control of damping-off as described in Example 16. There were almost twice as many healthy seedlings in the *P. oxalicum*-pellet treated replicates as in the control treatments.

Pellets containing *Penicillium oxalicum* as prepared in Example 12 were tested for control of damping-off as described in Example 16. There were more than twice as many healthy seedlings in the *P. oxalicum*-pellet treatments as in those treated with pellets containing no fungal propagules.

EXAMPLE 20

Pellets containing *Trichoderma viride* as prepared in Example 13 were tested for control of damping-off as described in Example 16. There were twice as many healthy seedlings in the *T. viride*-pellet treatments as in those treated with pellets containing no fungal propagules.

EXAMPLE 21

Pellets containing *Trichoderma viride* as prepared in Example 14 were tested for control of damping-off as described in Example 16. There were more than twice as many healthy seedling in the *T. viride*-pellet treatments as in those treated with pellets containing no fungal propagules.

TABLE 1

SURVIVAL OF FUNGI USED AS BIOLOGICAL CONTROL AGENTS IN ALGINATE PELLETS AT ROOM TEMPERATURE

| Isolate and Propagule | Gellant | Concentration Before Pellet Formation (Equivalent Propagules/Pellet) | Survival During Pellet Formation (% Per Pellet) | $ES_{50}{}^a$ (Weeks) | Propagule Viability After 12 Weeks | |
|---|---|---|---|---|---|---|
| | | | | | Per g $\times 10^3$ | Per Pellet |
| *Gliocladium virens* | | | | | | |
| (Gl-3) Conidia | $CC^b$ | $6.7 \times 10^{5c}$ | 89.0 | 0.2 | 0.18 | 12 |
| | | $2.0 \times 10^5$ | 40.0 | 0 | 0.45 | 30 |
| | | $3.4 \times 10^4$ | 78.4 | 0.2 | 1.10 | 73 |
| | CG | $3.4 \times 10^4$ | 57.0 | 2.2 | $35.00*^d$ | $2.3 \times 10^3$ |
| *Penicillum oxalicum* | | | | | | |
| Conidia | CC | $4.3 \times 10^6$ | 100.0 | 0 | 0.08 | 5 |
| | | $4.4 \times 10^5$ | 100.0 | 0 | 0.12 | 8 |
| | | $9.3 \times 10^3$ | 100.0 | 1.9 | 0.05 | 3 |
| | CG | $9.3 \times 10^3$ | 100.0 | >12.0 | 8.50* | $5.7 \times 10^2$ |
| *Talaromyces flavus* | | | | | | |
| (Tfl) Ascospores | CC | $2.7 \times 10^4$ | 100.0 | >12.0 | 220.00 | $1.5 \times 10^4$ |
| | | $3.3 \times 10^3$ | 100.0 | >12.0 | 17.50 | $1.2 \times 10^3$ |
| | | $1.7 \times 10^2$ | 100.0 | 6.4 | 5.50 | $3.7 \times 10^2$ |
| | CG | $1.7 \times 10^2$ | 100.0 | >12.0 | 390.00* | $2.6 \times 10^4$ |
| Conidia | CC | $1.5 \times 10^6$ | 100.0 | 0 | 0.12 | 8 |
| | | $1.3 \times 10^4$ | 100.0 | 5.4 | 0 | 0 |
| | | $1.5 \times 10^3$ | 100.0 | 0 | 0 | 0 |
| | CG | $1.5 \times 10^3$ | 100.0 | 8.6 | 405.00* | $2.7 \times 10^4$ |
| *Talaromyces flavus* | | | | | | |
| (Tfl-l) Ascospores | CC | $2.7 \times 10^4$ | 100.0 | 0.7 | 0 | 0 |
| | | $2.0 \times 10^3$ | 100.0 | 4.0 | 0 | 0 |
| | | $3.9 \times 10^2$ | 100.0 | 5.5 | 2.00 | $1.3 \times 10^2$ |
| | CG | $3.9 \times 10^2$ | 100.0 | >12.0 | 255.00* | $1.7 \times 10^4$ |
| *Talaroymces flavus* | | | | | | |
| (Tfl-1) Conidia | CC | $2.0 \times 10^7$ | 100.0 | 0 | 0.10 | 7 |
| | | $2.6 \times 10^5$ | 100.0 | 9.7 | 0 | 0 |
| | | $7.3 \times 10^3$ | 100.0 | 0 | 0.20 | 13 |
| | CG | $7.3 \times 10^3$ | 100.0 | 2.8 | 255.00* | $1.7 \times 10$ |
| *Trichoderma viride* | | | | | | |
| (T-1-R9) Conidia | CC | $6.8 \times 10^6$ | 100.0 | 2.7 | 0 | 0 |
| | | $6.7 \times 10^5$ | 100.0 | 2.7 | 0 | 0 |
| | | $6.6 \times 10^4$ | 100.0 | 2.5 | 0 | 0 |

TABLE 1-continued

SURVIVAL OF FUNGI USED AS BIOLOGICAL CONTROL
AGENTS IN ALGINATE PELLETS AT ROOM TEMPERATURE

| Isolate and Propagule | Gellant | Concentration Before Pellet Formation (Equivalent Propagules/Pellet) | Survival During Pellet Formation (% Per Pellet) | $ES_{50}{}^a$ (Weeks) | Propagule Viability After 12 Weeks | |
|---|---|---|---|---|---|---|
| | | | | | Per g × $10^3$ | Per Pellet |
| | GC | $6.6 \times 10^4$ | 100.0 | >12.0 | 940.00* | $6.4 \times 10^4$ |

$^a ES_{50}$ = Effective Survival 50% indicates the length of time after drying for loss of 50% of the viable propagules.
$^b$CC = calcium chloride; CG = calcium gluconate.
$^c$Data from one experiment.
$^d$Values marked by an asterisk are significantly greater (P ≦ 0.05) compared to population values for their respective initial, air-dry concentrations.

We claim:

1. A method for producing pellets containing living fungi inoculum for control of soilborne plant diseases comprising:
    (a) selecting and growing living fungi from the group consisting of: Gliocladium virens isolate Gl3, Penicillium oxalicum isolate Windels, Talaroymces flavus isolate Tf-1, Talaromyces flavus biotype Tfl-1, Trichoderma viride biotype T-1-R9, for sufficient time to be used as inoculum;
    (b) harvesting and homogenizing the living fungal propagules of (a) for sufficient time to uniformly mix the propagules;
    (c) diluting the living fungal propagule homogenate with a sodium alginate solution of a sufficient concentration to effect subsequent gelation;
    (d) adding dropwise the product of (c) into an aqueous solution of of a calcium salt, said calcium salt selected from the group consisting of calcium chloride and calcium gluconate, thereby forming alginate gel pellets containing living fungi dispersed throughout.

2. The method of claim 1 including the addition of a filler material to the sodium alginate solution of step (c).

3. The method of claim 1 wherein the living fungus is Gliocladium virens isolate Gl-3, and is inoculum to control damping-off diseases.

4. The method of claim 1 wherein the living fungus is Penicillium oxalicum isolate Windels and is inoculum to control damping-off diseases.

5. The method of claim 1 wherein the living fungus is Talaromyces flavus isolate Tf-1, and is inoculum to control Verticillium wilt disease.

6. The method of claim 1 wherein the living fungus is Talaromyces flavus biotype Tfl-1, and is inoculum to control Verticillium wilt disease.

7. The method of claim 1 wherein the living fungus is Trichoderma viride biotype T-1-R9, and is inoculum to control damping-off diseases.

8. The method of claim 1 including the additional step of drying the alginate gel pellets containing the living fungus dispersed throughout thereby transforming the gel beads into granules or pellets containing living fungus.

9. The method of claim 1 wherein the sodium alginate solution is in concentrations of from about 0.5% to 2.0% w/v.

10. The method of claim 2 wherein the filler material is pyrophyllite and is used in concentrations of from about 5% to 20% of the total weight of the solution.

11. A method for controlling soilborne plant diseases in an agricultural field comprising:
    applying living fungus-containing alginate gel pellets to an agricultural field infested with soilborne plant diseases, wherein said living fungus reproduces and controls said soilborne plant diseases, said fungus selected from the group consisting of: Gliocladium virens isolate Gl-3, Penicillium oxalicum isolate Windles, Talaromyces Flavus isolate Tl-1, Talaromyces biotype Tfl-1 and Trichoderma viride biotype T-1-R9.

12. The method of claim 11 wherein alginate gel pellets containing living fungus Gliocladium virens isolate Gl-3 are applied to an agricultural field infested with Pythium and Rhizoctoni so that said G. virens may reproduce and control damping-off diseases.

13. A method of claim 11 wherein the alginate gel pellets containing living fungus Penicillium oxalicum isolate Windels are applied to an agricultural field to control Pythium and Rhizoctonia so that said P. oxalicium may reproduce and control damping-off diseases.

14. The method of claim 11 wherein the alginate gel pellets containing the living fungus Talaromyces flavus isolate Tf-1 are applied to an agricultural field infested with Verticillium dahliae so that said T. flavus may reproduce and control Verticillium wilt disease.

15. The method of claim 11 wherein the alginate gel pellets containing the living fungus Talaromyces flavus biotype Tfl-1 are applied to an agricultural field infested with Verticillium dahalie so that said T. flayus may reproduce and control Verticillium wilt disease.

16. The method of claim 11 wherein the alginate gel pellets containing the living fungus Trichoderma viride biotype T-1-R9 are applied to an agricultural field infested with Pythium and Rhizoctonia so that said T. viride may reproduce and control damping-off diseases.

* * * * *